United States Patent [19]

Norris

[11] Patent Number: 5,039,812

[45] Date of Patent: Aug. 13, 1991

[54] INSENSITIVE HIGH DENSITY EXPLOSIVE

[75] Inventor: William P. Norris, Ridgecrest, Calif.

[73] Assignee: The United States of America as represented by the Secretary of the Navy, Washington, D.C.

[21] Appl. No.: 259,203

[22] Filed: Apr. 13, 1981

[51] Int. Cl.[5] ............................................ C07D 271/12
[52] U.S. Cl. ...................................... 548/126; 149/92
[58] Field of Search .................... 149/92; 548/125, 126

[56] References Cited

U.S. PATENT DOCUMENTS

| H476 | 6/1988 | Norris | 548/126 |
|---|---|---|---|
| 3,711,609 | 1/1973 | Lehmann et al. | 548/125 X |
| 3,832,249 | 8/1974 | Homewood et al. | 548/125 X |
| 4,754,040 | 6/1988 | Chafin et al. | 548/126 |

Primary Examiner—Richard D. Lovering
Assistant Examiner—John M. Covert
Attorney, Agent, or Firm—Melvin J. Sliwka; Sol Sheinbein

[57] ABSTRACT

The compound, 5,7-diamino-4,6-dinitro-benzofuroxan is formed by (1) forming a reaction mixture containing 4,6-dinitro benzofuroxan, $KHCO_3$, $NH_2OH$ HCl and water; (2) forming the potassium salt of the desired compound by adding KOH to the reaction mixture; and (3) adding HCl to replace the potassium ion of the salt with hydrogen. The compound is useful as an explosive.

5 Claims, No Drawings

INSENSITIVE HIGH DENSITY EXPLOSIVE

BACKGROUND OF THE INVENTION

1. Field of the Invention

This invention relates to explosives. More specifically, this invention relates to a chemical compound which is useful as an explosive and to a method for the preparation thereof.

2. Description of the Prior Art

Organic chemical compounds which contain nitro groups are well known to be explosives. A typical example is the well known trinitrotoluene (TNT). Another is triaminotrinitobenzene (TATB) and there are many more.

Despite the availability of many explosive nitro containing organic compounds, the search for new ones goes continually on. The armed forces and workers in various civilian occupations such as mining and road building have need for ever more powerful higher density, lower sensitivity explosives.

SUMMARY OF THE INVENTION

This invention provides an insensitive, high density explosive that is more powerful than triaminotrinstrabenzene (TATB). The explosive provided by this invention is 5,7-diamino-4,6-dinitrobenzofuroxan. It is prepared by stirring 4,6-dinitrobenzofuroxan with $KHCO_3$ and $NH_2OH.HCl$ in water for about 3.5 to 4.5 hours at 25° C., cooling the thus formed mixture to 0° C., adding KOH and stirring for about 3.5 hours whereby a solid potassium salt of 5,7-diamino-4,6-dinitrobenzofuroxan is formed. This salt is then suspended in water and stirred with HCl to form the explosive.

DESCRIPTION OF THE PREFERRED EMBODIMENT

The preferred embodiment of this invention may be readily understood by referring to the follow specific example.

EXAMPLE 4,6-Dinitrobenzofuroxan (7.2 g) was dissolved in 100 ml. of $H_2O$. $KHCO_3$ (14.4 g) and $NH_2OH.HCl$ (8.3 g) were added to the solution and the thus formed reaction mixture was stirred for 3.5 hours at 25° C. The reaction mixture was then cooled to about 0° C. and 100 ml. of 4N KOH (also cooled to ~0° C.) was added. The reaction vessel was immersed in ice water and stirring was continued for another 3.5 hours. (The addition of the KOH produced a mixture which was 2 N in KOH.) A yellow solid precipitate formed in the reaction vessel. The yellow solid wa the potassium salt of 5,7-diamino-4,6-dinitrobenzofuroxan.

The yellow solid was separated from the reaction mixture and suspended in water at room temperature. An excess of 1N HCl was added and this newly formed reaction mixture was stirred for about 1 hour. The HCl replaced the potassium ion of the salt with hydrogen and produced the compound of this invention, 5,7-diamino-4,6-dinitrobenzofuroxan. Analysis of the compound by NMR at 0° C. in dimethylsulfoxide (TMX standard) showed $NH_2$-5, 10.2 and 9.22δ; $NH_2$-7, 10.848 δ and 10.02 δ. Elemental analysis was as follows: Calcd: for $C_6H_4N_6O_6$; C, 28.13; H, 1.57; N, 32.81; O, 37.48; Found: C, 28.02; H, 1.45; N, 32.72. The compound had a melting point of 294° C.

To utilize the compound of this invention as an explosive, one may compact the material by means of pressure and detonate with any standard detonator. Alternatively, the explosive powder may be utilized as an explosive filler in a standard binder material such as hydroxyl terminated polybutadiene and the resulting plastic bonded explosive detonated by means of any standard detonator.

While the foregoing specific example sets forth certain specific reaction times and temperatures, these may be varied somewhat with no ill effects. For example, the temperature at which the first reaction mixture (4,6-dinitrobenzofuroxan plus $H_2O + KHCO_3 + NH_2OH.HCl$) is held may be varied in the range of from about 20° C. to about 30° C. and the time it is stirred may be varied in the range of from about 3.5 to an indeterminately large number of hours. The 0° C. temperature used after the addition of KOH is also not absolutely necessary. A temperature in the range of from about −5° C. to about +5° C. is suitable and, as in the case prior to the addition of KOH, the mixture may be stirred for a much greater length of time than 3.5 hours. The reaction time after HCl is added can also be increased greatly and the temperature may be varied in the range of from about 10° to about 30° C. An equimolar amount of HCl could be used in lieu of the excess set forth in the specific example. In short, the specific example merely sets forth the best mode for making the compound that is presently known to the inventor.

Tests have indicated that the explosive of this invention more powerful than TATB.

What is claimed is:

1. 5,7-Diamino-4,6-dinitrobenzofuroxan.

2. A method for preparing 5,7-diamino-4,6-dinitrobenzofuroxan comprising the steps of:
   A. forming a reaction mixture by adding 4,6-dinitrobenzofuroxan, $KHCO_3$ and $NH_2OH.HCl$ to $H_2O$ and stirring;
   B. cooling the mixture to from about −5° C. to about +5° C., adding KOH and stirring to form the potassium salt of 5,7-diamino-4,6-dinitrobenzofuroxan; and
   C. adding HCl to said salt to form said 5,7-diamino-4,6-dinitrobenzofuroxan.

3. A method according to claim 2 wherein step A is carried out at 25° C. for 3.5 hours.

4. A method according to claim 3 wherein step B is carried out at 0° C. for 3.5 hours.

5. A method according to claim 4 wherein step C is carried our by adding an excess of HCl and stirring for about 1 hour.

* * * * *